(12) United States Patent
Pandolfi et al.

(10) Patent No.: US 11,499,152 B2
(45) Date of Patent: Nov. 15, 2022

(54) INHIBITORS OF MICRO-RNA 22

(71) Applicants: Beth Israel Deaconess Medical Center, Boston, MA (US); Aalborg Univeristy, Aalborg (DK)

(72) Inventors: Pier Paolo Pandolfi, Boston, MA (US); Riccardo Panella, Boston, MA (US); Sakari Kauppinen, Aalborg (DK); Andreas Petri, Aalborg (DK)

(73) Assignees: Beth Israel Deaconess Medical Center, Boston, MA (US); Aalborg University, Aalborg (DK)

( * ) Notice: Subject to any disclaimer, the term of this patent is extended or adjusted under 35 U.S.C. 154(b) by 0 days.

(21) Appl. No.: 16/979,782

(22) PCT Filed: Mar. 14, 2019

(86) PCT No.: PCT/US2019/022351
§ 371 (c)(1),
(2) Date: Sep. 10, 2020

(87) PCT Pub. No.: WO2019/178411
PCT Pub. Date: Sep. 19, 2019

(65) Prior Publication Data
US 2021/0017521 A1    Jan. 21, 2021

Related U.S. Application Data

(60) Provisional application No. 62/642,934, filed on Mar. 14, 2018.

(51) Int. Cl.
*C07H 21/04* (2006.01)
*C12N 15/113* (2010.01)
*A61K 31/713* (2006.01)

(52) U.S. Cl.
CPC .......... *C12N 15/113* (2013.01); *A61K 31/713* (2013.01); *C12N 2310/11* (2013.01); *C12N 2310/113* (2013.01); *C12N 2310/14* (2013.01); *C12N 2310/141* (2013.01); *C12N 2310/3231* (2013.01); *C12N 2310/344* (2013.01); *C12N 2320/50* (2013.01)

(58) Field of Classification Search
CPC .......................... C12N 15/113; C12N 2310/141
See application file for complete search history.

(56) References Cited

U.S. PATENT DOCUMENTS

| | | | | |
|---|---|---|---|---|
| 8,288,356 | B2 * | 10/2012 | Obad | C12N 15/111 514/44 A |
| 10,358,643 | B2 * | 7/2019 | Albaek | A61P 43/00 |
| 2007/0213292 | A1 * | 9/2007 | Stoffel | C12N 15/113 514/44 A |
| 2010/0004320 | A1 | 1/2010 | Elmen et al. | |
| 2012/0148664 | A1 | 6/2012 | Dalby et al. | |
| 2015/0111949 | A1 | 4/2015 | Pandolfi et al. | |

FOREIGN PATENT DOCUMENTS

| | | | | |
|---|---|---|---|---|
| WO | WO 2007/112754 | A2 | 10/2007 | |
| WO | WO 2013/181613 | A1 | 12/2013 | |
| WO | WO 2016/127002 | A1 | 8/2016 | |
| WO | WO 2016/149358 | A1 * | 9/2016 | ........... C12N 15/113 |

OTHER PUBLICATIONS

International Search Report & Written Opinion, PCT Application No. PCT/US19/22351, dated Jul. 29, 2019, 12 pages.
Lennox, et al., "Chemical modification and design of anti-miRNA oligonucleotides," Gene Therapy, vol. 18, No. 12, pp. 1111-1120, Jul. 14, 2011.
Gurha, "MicroRNAs in cardiovascular disease," Current Opinion in Cardiology, vol. 31, No. 3, pp. 249-254, May 3, 2016.

* cited by examiner

*Primary Examiner* — Amy H Bowman
(74) *Attorney, Agent, or Firm* — Morgan, Lewis & Bockius LLP (57) ABSTRACT

The present disclosure provides compositions and methods that inhibit the activity of microRNAs, for example miR-22.

5 Claims, 10 Drawing Sheets

Specification includes a Sequence Listing.

FIGURE 1

Design anti-miR-22 LNA

```
hsa-miR-22   5'  AAGCUGCCAGUUGAAGAACUGU  3'
                   ||||||||
CRM0008      3'  TCGACGGT                5'
CRM0009          TCgAcGgtCAacTtC
CRM0010          TCgACGgtCAacTTC                All anti-miR-22 oligos are
CRM0011          TCgACGgtCaACTtCT               designed with mix-mer
CRM0012          TCgACGGtCaacTtCT               strategy
CRM0013          TCgACGgTcaACTtCT
CRM0014          TCgACGgTcaACTtcTT
CRM0015          TCGaCGgtCaacTtctTG
CRM0016          GCgATGatTgATAaGC
CRM0017          GCgATGatTgATAaGC-FAM labelled  Scramble
```

Capital Letter LNA
Lower case DNA

Dot Blot Assay for 5hmC in MCF7 48h transfection

Day 8, MEF WT treated with 500nM LNA (un-assisted uptake)

FIGURE 14

FIGURE 15

INHIBITORS OF MICRO-RNA 22

PRIORITY

This application claims the benefit of, and claims priority to, U.S. Provisional Application No. 62/642,934, filed Mar. 14, 2018, the contents of which is hereby incorporated by reference in its entirety.

FIELD OF THE DISCLOSURE

The disclosure relates to the agents that modulate the activity or expression of microRNAs.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BID-005PC2_ST25.txt; date created: Mar. 14, 2019; file size: 2,976 bytes).

BACKGROUND

MicroRNAs (miRNA or miR) are nucleic acid molecules that regulate the expression of target genes. MiRNAs are typically short (typically 18-24 nucleotides) and act as repressors of target mRNAs by promoting their degradation, when their sequences are perfectly complementary, and/or by inhibiting translation, when their sequences contain mismatches. Functional analyses of miRNAs have revealed that these small non-coding RNAs contribute to different physiological and metabolic processes, including regulating genes associated with various diseases or disorders.

As such, there is a need for compositions and method that regulate miRs.

SUMMARY

The present disclosure provides new compositions and methods for inhibiting miR-22, for example by inhibiting microRNA expression and/or activity. Such inhibition can be mediated by sequence specific chemically modified oligonucleotides, including for example, locked nucleic acid (LNA).

In one aspect, the present invention provides a miR-22 inhibitory composition. The composition comprises a nucleic acid having a sequence comprising tggcagct (SEQ ID NO: 2) and comprising at least one locked nucleic acid (LNA) modification.

In embodiments, the nucleic acid comprises LNA modifications at positions 7 and 8 of tggcagct (SEQ ID NO: 2). In embodiments, the nucleic acid comprises about 8 to about 12 LNA modifications. In embodiments, the nucleic acid comprises no less than 4 LNA modifications. In embodiments, the nucleic acid comprises no more than four sequential LNA modifications.

In embodiments, the nucleic acid comprises a nucleic acid having a sequence selected from: tggcagct (SEQ ID NO: 2), cttcaactggcagct (SEQ ID NO: 3), tcttcaactggcagct (SEQ ID NO: 4), ttcttcaactggcagct (SEQ ID NO: 5), and gttcttcaactggcagct (SEQ ID NO: 6). In embodiments, the nucleic acid comprises about 8 to about 12 LNA modifications, e.g., about 8 to about 10 LNA modifications. In embodiments, the nucleic acid comprises about 8, or about 9, or about 10, or about 11, or about 12 LNA modifications.

In embodiments, the nucleic acid comprises tggcagct (SEQ ID NO: 2), and at least 6 LNA modifications.

In embodiments, the nucleic acid comprises tggcagct (SEQ ID NO: 2), and at least 8 LNA modifications.

In embodiments, the nucleic acid comprises cttcaactggcagct (SEQ ID NO: 3), and at least 6 LNA modifications, at least 8 LNA modifications, or at least 10 LNA modifications. In embodiments, the nucleic acid comprises cttcaactggcagct (SEQ ID NO: 3), and 8 LNA modifications, said modifications being at positions 1, 3, 6, 7, 10, 12, 14, and 15. In embodiments, the nucleic acid comprises cttcaactggcagct (SEQ ID NO: 3), and 10 LNA modifications, said modifications being at positions 1, 2, 3, 6, 7, 10, 11, 12, 14, and 15.

In embodiments, the nucleic acid comprises tcttcaactggcagct (SEQ ID NO: 4), and at least 8 LNA modifications, at least 10 LNA modifications, or at least 11 LNA modifications. In embodiments, the nucleic acid comprises tcttcaactggcagct (SEQ ID NO: 4), and 10 LNA modifications, said modifications being at positions 1, 2, 4, 8, 10, 11, 12, 13, 15, and 16. In embodiments, the nucleic acid comprises tcttcaactggcagct (SEQ ID NO: 4), and 11 LNA modifications, said modifications being at positions 1, 2, 4, 5, 6, 8, 11, 12, 13, 15, and 16. In embodiments, the nucleic acid comprises tcttcaactggcagct (SEQ ID NO: 4), and 11 LNA modifications, said modifications being at positions 1, 2, 4, 5, 6, 9, 11, 12, 13, 15, and 16.

In embodiments, the nucleic acid comprises ttcttcaactggcagct (SEQ ID NO: 5), and at least 10 LNA modifications or at least 11 LNA modifications. In embodiments, the nucleic acid comprises ttcttcaactggcagct (SEQ ID NO: 5), and 11 LNA modifications, said modifications being at positions 1, 2, 5, 6, 7, 10, 12, 13, 14, 16, and 17.

In embodiments, the nucleic acid comprises gttcttcaactggcagct (SEQ ID NO: 6), and at least 9 LNA modifications or at least 10 LNA modifications. In embodiments, the nucleic acid comprises gttcttcaactggcagct (SEQ ID NO: 6), and 9 LNA modifications, said modifications being at positions 1, 2, 6, 10, 13, 14, 16, 17, and 18.

In another aspect, the present invention provides a pharmaceutical composition comprising the nucleic acid of the above aspect or any of the above embodiments and a pharmaceutically acceptable excipient or carrier.

In yet another aspect, the present invention provides a vector or a plasmid comprising a nucleic acid of the above aspect or any of the above embodiments.

An aspect of the present invention provides a host cell comprising a nucleic acid of the above aspect or any of the above embodiments.

Another aspect of the present intention provides a method for inhibiting miR-22. The method comprising contacting miR-22 with a composition comprising an inhibitor of miR-22 that is a nucleic acid of the above aspect or any of the above embodiments.

Any aspect or embodiment described herein can be combined with any other aspect or embodiment as disclosed herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 6A-C show an unassisted uptake of anti-miR-22 LNAs in MCF7 affects target protein level. FIGS. 6A and 6B are western blot images showing TET2 expression relative to HSP-90 control. FIG. 6C is a bar graph showing TET2 protein expression. In FIG. 6C, the order of data in the bar graphs, reading from left to right, is SCR (in black), 25 nM (in light grey), and 100 nM (in dark grey).

FIG. 10A-B are line graphs showing an in vivo pharmacological inhibition of miR-22 prevents mice from becoming obese. FIG. 10A shows the final percentage body increase. FIG. 10B shows in vivo silencing of miR-22 in DIO mice. In both figures, at the final time points, the order of data going from top to bottom is Vehicle (in green), SCR (in red), and anti-miR-22 (in blue).

FIG. 14 is an Oil-Red 0 staining (FIG. 14A) and a bar graph (FIG. 14B) showing that anti-miR-22 treatment in Human Primary Mesenchymal cells cultured in Adipo differentiation media for 2 weeks with or without LNA anti-miR-22. Un-assisted uptake 500 nM (LNAs added every 2 days). In FIG. 14B, the data in the right (red) bars in each bar graph is for the with LNA #10-treated cells.

DETAILED DESCRIPTION OF THE DISCLOSURE

The present disclosure provides new compositions and methods for inhibiting miR-22, for example by inhibiting microRNA expression and/or activity.

Without being bound by theory, mature miRNAs are believed to be generated by pol II or pol III and arise from initial transcripts termed pri-miRNAs. These pri-miRNAs are frequently several thousand bases long and are therefore processed to make much shorter mature miRNAs. These pri-miRNAs may be multicistronic and result from the transcription of several clustered sequences that organize what may develop into many miRNAs. The processing to yield miRNAs may be two-steps. First, pri-miRNAs may be processed in the nucleus by the RNase Drosha into about 70- to about 100-nucleotide hairpin-shaped precursors (pre-miRNAs). Second, after transposition to the cytoplasm, the hairpin pre-miRNAs may be further processed by the RNase Dicer to produce a double-stranded miRNA. The mature miRNA strand may then be incorporated into the RNA-induced silencing complex (RISC), where it may associate with its target mRNAs by base-pair complementarity and lead to suppression of protein expression. The other strand of the miRNA duplex that is not preferentially selected for entry into a RISC silencing complex is known as the passenger strand or minor miRNA or star (*) strand. This strand may be degraded. It is understood that, unless specified, as used herein a miRNA may refer to pri- and/or pre- and/or mature and/or minor (star) strand and/or duplex version of miRNA.

In some embodiments, miRNA genes may be located within introns of protein-coding genes or within introns or exons of noncoding transcriptional units. The expression of intronic miRNAs may coincide with that of the hosting transcriptional units because they are typically oriented in the same direction and are coordinately expressed with the pre-mRNAs in which they reside.

In some embodiments, miRNAs may bind to sequences within the 3' untranslated region (3'UTR) of target gene transcripts. In some embodiments, miRNAs may bind to sequences outside of the 3'UTR of target gene transcripts. In some embodiments, miRNAs may bind to both within and outside the 3'UTR of target gene transcripts.

In some embodiments, nucleotide pairing between the second and seventh nucleotides of the miRNA (the miRNA seed sequence) and the corresponding sequence along the target 3'UTR (seed match) may occur for target recognition. Accordingly, the binding between miRNA and target may comprise about a 5 nucleotide base pairing. Additionally, the binding between miRNA and target may comprise more than a 5 nucleotide base pairing. In some embodiments, the binding between an miRNA and the gene that it regulates may be mediated by the miRNA binding up to 2, up to 4, up to 6, up to 8, or up to 10 sites of the target nucleic acid.

MiR-22

MiR-22 is highly conserved across many vertebrate species, including chimp, mouse, rat, dog and horse. This level of conservation suggests functional importance. MiR-22 was previously identified as having a role in erythrocyte maturation and later as having a role in oncogenesis. MiR-22 directly targets phosphatase and tensin homolog (PTEN) and tet methylcytosine dioxygenase (TET) to promote tumorigenesis, metastasis and metabolic disorders. In some embodiments, the nucleic acids of the present invention increase the activity and/or expression of PTEN and/or TET2.

The predicted miR-22 hairpin precursor is contained entirely within exon 2 of a noncoding transcript, C17orf91, and the splicing pattern is generally conserved in human and mouse, despite the lack of protein-coding potential. See Rodriguez et al., Identification of mammalian microRNA host genes and transcription units. Genome Res. 2004 October; 14(10A):1902-10. Deletion of exon 2 of C17orf91 encompassing mir-22 in mouse models has revealed that miR-22 may play a role in cardiac hypertrophy and remodeling by targeting SIRT1 (NAD-dependent deacetylase sirtuin-1), HDAC4 (histone deacetylase 4), PURB (purine-rich element binding protein B) and PTEN. See Gurha et al., Targeted deletion of microRNA-22 promotes stress-induced cardiac dilation and contractile dysfunction. Circulation. 2012 Jun. 5; 125(22):2751-61; Huang et al., MicroRNA-22 regulates cardiac hypertrophy and remodeling in response to stress. Circ Res. 2013 Apr. 26; 112(9): 1234-43.

Inhibitors of miR-22

In embodiments, an inhibitor of miRNA is a nucleic acid that acts as an antisense oligonucleotide. Nucleic acids of the present invention can include ribonucleotides or deoxyribonucleotides or a combination thereof. Nucleic acids of the present invention may have at least one chemical modification (non-limiting examples are sugar or backbone modifications, e.g., a Locked Nucleic Acid (LNA)).

In embodiments, the sequence of a nucleic acid that inhibits miR-22 is conserved across species. In embodiments, the sequence of the nucleic acid is complementary, in part, to the sequence of human miR-22. In embodiments, the inhibitor is selected to reduce the expression and/or activity of the target miR-22 in a cell or a subject.

In embodiments, nucleic acids of the present invention inhibit human miR-22. In embodiments, human miR-22 comprises or consists of AAGCUGCCAGUU-GAAGAACUGU (SEQ ID NO: 1).

In embodiments, the nucleic acids of the present invention are about 8 to about 20 residues in length (e.g., about 8-18, or about 8-16, or about 8-14, or about 8-12, or about 8-10, or about 10-18, or about 10-16, or about 10-14, or about 10-12 residues in length). In embodiments, the nucleic acids are about 8, or about 9, or about 10, or about 11, or about 12 residues in length.

In embodiments, nucleic acids of the present invention bind with complete homology to a portion of miR-22. For example, a nucleic acid of the present invention may be 18 residues in length and each of the 18 residues is complementary to a nucleotide of miR-22. Alternately, the nucleic acids of the present invention bind with complete homology to a portion of miR-22. For example, for a nucleic acid of the present invention may be 16 residues in length and only 15 or fewer of the residues are complementary to a nucleotide of miR-22.

In embodiments, a nucleic acid of the present invention differs from a portion of miR-22 at one position, at two positions, at three positions, at four positions, at five positions, or at more than five positions.

In embodiments, a nucleic acid of the present invention binds to miR-22 with sufficient affinity to inhibit it. In embodiments, the nucleic acids bind to miR-22 with a high affinity (e.g. nM affinity). Thus, a nucleic acid of the present invention binds to miR-22 with a high affinity even if it differs from a portion of miR-22 at one or more positions.

A nucleic acid of the present invention may have a sequence comprising tggcagct (SEQ ID NO: 2) and comprising at least one locked nucleic acid (LNA) modification.

In a locked nucleic acid (LNA) the nucleic acid's ribose moiety is modified with an extra bridge connecting the 2' oxygen and 4' carbon, which locks the ribose in the 3'-endo conformation. Nucleic acids of the present invention, and comprising LNAs, provide for cost-effective agents that can be delivered efficiently and possess sufficient bioavailability for the treatment and prevention of various disorders.

In embodiments, a nucleic acid of the present invention includes at least 2 LNA modifications towards its 3' end (e.g., about 2, or about 3, or about 4, or about 5 modifications towards its 3' end). In embodiments, the nucleic acid comprises tggcagct (SEQ ID NO: 2), and at least 6 LNA modifications or at least 8 LNA modifications.

For example, the nucleic acid comprises LNA modifications at positions 7 and 8 of tggcagct (SEQ ID NO: 2). In embodiments, a nucleic acid of the present invention includes no more than 4 sequential LNA modifications (e.g., only 2, or 3, or 4 sequential LNA modifications). In embodiments, a nucleic acid of the present invention includes no more than 3 sequential unmodified residues (e.g., only 3, or 2, or 1 unmodified residues). In embodiments, a nucleic acid of the present invention includes no less than 4 LNA modifications. In embodiments, the nucleic acid comprises about 8 to about 12 LNA modifications, e.g., about 8, or about 9, or about 10, or about 11, or about 12 LNA modifications.

In embodiments, the nucleic acid comprises or consists of a nucleic acid having a sequence selected from: tggcagct (SEQ ID NO: 2), cttcaactggcagct (SEQ ID NO: 3), tcttcaactggcagct (SEQ ID NO: 4), ttcttcaactggcagct (SEQ ID NO: 5), and gttcttcaactggcagct (SEQ ID NO: 6). In embodiments, the nucleic acid comprises a nucleic acid having a sequence selected from: tggcagct (SEQ ID NO: 2), cttcaactggcagct (SEQ ID NO: 3), tcttcaactggcagct (SEQ ID NO: 4), ttcttcaactggcagct (SEQ ID NO: 5), and gttcttcaactggcagct (SEQ ID NO: 6) and comprising about 8 to about 12 LNA modifications, e.g., about 8, or about 9, or about 10, or about 11, or about 12 LNA modifications.

In embodiments, the nucleic acid comprises or consists of cttcaactggcagct (SEQ ID NO: 3), and at least 6 LNA modifications, at least 8 LNA modifications, or at least 10 LNA modifications. In embodiments, the nucleic acid comprises or consists of cttcaactggcagct (SEQ ID NO: 3), and 8 LNA modifications, said modifications being at positions 1, 3, 6, 7, 10, 12, 14, and 15; for example, the nucleic acid comprises or consists of the sequence CtTcaACtgGcAgCT (SEQ ID NO: 7), where capital letters are LNA modified and lower case are unmodified. In embodiments, the nucleic acid comprises or consists cttcaactggcagct (SEQ ID NO: 3), and 10 LNA modifications, said modifications being at positions 1, 2, 3, 6, 7, 10, 11, 12, 14, and 15; for example, the nucleic acid comprises or consists of the sequence CTTcaACtgGCAgCT (SEQ ID NO: 8), where capital letters are LNA modified and lower case are unmodified.

In embodiments, the nucleic acid comprises or consists of tcttcaactggcagct (SEQ ID NO: 4), and at least 8 LNA modifications, at least 10 LNA modifications, or at least 11 LNA modifications. In embodiments, the nucleic acid comprises or consists of tcttcaactggcagct (SEQ ID NO: 4), and 10 LNA modifications, said modifications being at positions 1, 2, 4, 8, 10, 11, 12, 13, 15, and 16; for example, the nucleic acid comprises or consists of the sequence TCtTcaaCtGGCAgCT (SEQ ID NO: 10), where capital letters are LNA modified and lower case are unmodified. In embodiments, the nucleic acid comprises or consists of tcttcaactggcagct (SEQ ID NO: 4), and 11 LNA modifications, said modifications being at positions 1, 2, 4, 5, 6, 8, 11, 12, 13, 15, and 16; for example, the nucleic acid comprises or consists of the sequence TCtTCAaCtgGCAgCT (SEQ ID NO: 9), where capital letters are LNA modified and lower case are unmodified.

In embodiments, the nucleic acid comprises or consists of tcttcaactggcagct (SEQ ID NO: 4), and 11 LNA modifications, said modifications being at positions 1, 2, 4, 5, 6, 9, 11, 12, 13, 15, and 16; for example, the nucleic acid comprises or consists of the sequence TCtTCAacTgGCAgCT (SEQ ID NO: 11), where capital letters are LNA modified and lower case are unmodified.

In embodiments, the nucleic acid comprises or consists of ttcttcaactggcagct (SEQ ID NO: 5), and at least 10 LNA modifications or at least 11 LNA modifications. In embodiments, the nucleic acid comprises or consists of ttcttcaactggcagct (SEQ ID NO: 5), and 11 LNA modifications, said modifications being at positions 1, 2, 5, 6, 7, 10, 12, 13, 14, 16, and 17; for example, the nucleic acid comprises or consists of the sequence TTctTCAacTgGCAgCT (SEQ ID NO: 12), where capital letters are LNA modified and lower case are unmodified.

In embodiments, the nucleic acid comprises or consists of gttcttcaactggcagct (SEQ ID NO: 6), and at least 9 LNA modifications or at least 10 LNA modifications. In embodiments, the nucleic acid comprises or consists of gttcttcaactggcagct (SEQ ID NO: 6), and 9 LNA modifications, said modifications being at positions 1, 2, 6, 10, 13, 14, 16, 17, and 18; for example, the nucleic acid comprises or consists of the sequence GTtctTcaaCtgGCaGCT (SEQ ID NO: 13), where capital letters are LNA modified and lower case are unmodified.

In embodiments, the nucleic acid comprising a sequence listed above, may further include additional nucleotides 5' to a herein-listed sequence and/or include additional nucleotides 3' to a herein-listed sequence. The additional nucleotides may be unmodified or may be modified, e.g., LNA or an additional chemical modification.

In some embodiments, a nucleic acid of the present invention may further include additional chemical modification. As examples, the chemical modification is one or more of a phosphorothioate, 2'-O-Methyl, or 2'-O-Methoxyethyl, 2'-O-alkyl-RNA unit, 2'-OMe-RNA unit, 2'-amino-DNA unit, 2'-fluoro-DNA unit (including, but not limited to, a DNA analogue with a substitution to a fluorine at the 2' position (2' F)), LNA unit, PNA unit, HNA unit, INA unit, and a 2' MOE RNA unit.

Suitable nucleic acids can be comprised of one or more conformationally constrained or bicyclic sugar nucleoside modifications (BSN) that confer enhanced thermal stability to complexes formed between the oligonucleotide containing BSN and their complementary miRNA target strand. For example, in one embodiment, the nucleic acids contain at least one locked nucleic acid. Locked nucleic acids (LNAs) contain a 2'-0, 4'-C-methylene ribonucleoside (structure A) wherein the ribose sugar moiety is in a locked conformation. In another embodiment, the nucleic acids contain at least one 2',4'-C-bridged 2' deoxyribonucleoside (CDNA, structure B). See, e.g., U.S. Pat. No. 6,403,566 and Wang et al., (1999) Bioorganic and Medicinal Chemistry Letters, Vol. 9: 1147-1150, both of which are herein incorporated by reference in their entireties. In yet another embodiment, the nucleic acids contain at least one modified nucleoside having the structure shown in structure C. The nucleic acids targeting miRNAs that regulate fat related metabolism and synthesis pathway targets can contain combinations of BSN (LNA, CDNA, and the like) or other modified nucleotides, and ribonucleotides or deoxyribonucleotides.

Alternatively, the nucleic acids can comprise peptide nucleic acids (PNAs), which contain a peptide-based backbone rather than a sugar-phosphate backbone. Other modified sugar or phosphodiester modifications to the nucleic acids are also contemplated. By way of non-limiting examples, other chemical modifications can include 2'-o-alkyl (e.g., 2'-O-methyl, 2'-o-methoxyethyl), 2'-fluoro, and 4'-thio modifications, and backbone modifications, such as one or more phosphorothioate, morpholino, or phosphonocarboxylate linkages (see, e.g., U.S. Pat. Nos. 6,693,187 and 7,067,641, which are herein incorporated by reference in their entireties). In one embodiment, nucleic acids targeting oncogenic miRNAs contain 2'-O-methyl sugar modifications on each base and are linked by phosphorothioate linkages. Nucleic acids, particularly those of shorter lengths (e.g., less than 16 nucleotides, 7-8 nucleotides) can comprise one or more affinity enhancing modifications, such as, but not limited to, LNAs, bicyclic nucleosides, phosphonoformates, 2' o-alkyl modifications, and the like. In some embodiments, suitable nucleic acids are 2'-O-methoxyethyl gapmers which contain 2'-O-methoxyethyl-modified ribonucleotides on both 5' and 3' ends with at least ten deoxyribonucleotides in the center. These gapmers are capable of triggering RNase H-dependent degradation mechanisms of RNA targets. Other modifications of nucleic acids to enhance stability and improve efficacy, such as those described in U.S. Pat. No. 6,838,283, which is herein incorporated by reference in its entirety, are known in the art and are suitable for use in the methods of the invention. For instance, and not intending to be limiting, to facilitate in vivo delivery and stability, the nucleic acids can be linked to a steroid, such as cholesterol moiety, a vitamin, a fatty acid, a carbohydrate or glycoside, a peptide, or other small molecule ligand at its 3' end.

As used herein, substantially complementary refers to a sequence that is at least about 95%, 96%, 97%, 98%, 99%, or 100% complementary to a target polynucleotide sequence (non-limiting examples are mature, minor, precursor miRNA, or pri-miRNA sequence of, for example, miR-22).

In some embodiments, the nucleic acid of the present invention is an antagomir. Antagomirs are single-stranded, chemically-modified ribonucleotides that are at least partially complementary to miRNAs and therefore may silence them. See, e.g., Kriitzfeldt, et al., Nature (2005) 438 (7068): 685-9. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting can be about 15 to about 50 nucleotides in length, about 18 to about 30 nucleotides in length, and about 20 to about 25 nucleotides in length. The antagomirs can be at least about 75%, 80%, 85%, 90%, 95%, 96%, 97%, 98%, or 99% complementary to a mature or minor oncogenic miRNA sequence. In some embodiments, the antagomir may be substantially complementary to a mature or minor oncogenic miRNA sequence, that is at least about 95%, 96%, 97%, 98%, or 99% complementary to a target polynucleotide sequence. In other embodiments, the antagomirs are 100% complementary to a mature or minor oncogenic miRNA sequence.

Nucleic acids of the present invention may comprise a sequence that is substantially complementary to a precursor miRNA sequence (pre-miRNA) or primary miRNA sequence (pri-miRNA) of an oncogenic miRNA. In some embodiments, nucleic acids of the present invention comprises a sequence that is located outside the 3'-untranslated region of a target of that miRNA. In some embodiments, nucleic acids of the present invention comprises a sequence that is located inside the 3'-untranslated region of a target of that miRNA.

In embodiments, the nucleic acids have limited or no self-binding affinity. In embodiments, the nucleic acids have limited or no duplex structures. In embodiments, the nucleic acids have limited or no fold structures.

Any nucleic acids of the present invention can be delivered to a target cell by delivering to the cell an expression vector encoding the miRNA inhibitors or agonists. A vector is a composition of matter which can be used to deliver a nucleic acid of interest to the interior of a cell. Numerous vectors are known in the art, including, but not limited to, linear polynucleotides, polynucleotides associated with ionic or amphiphilic compounds, plasmids, and viruses. Thus, the term vector includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms expression construct, expression vector, and vector are used interchangeably to demonstrate the application of the invention in a general, illustrative sense, and are not intended to limit the invention.

In one embodiment, an expression vector for expressing a nucleic acid of the present invention comprises a promoter operably linked to a polynucleotide encoding the nucleic acid of the present invention. The phrase operably linked or under transcriptional control as used herein means that the promoter is in the correct location and orientation in relation to a polynucleotide to control the initiation of transcription by RNA polymerase and expression of the polynucleotide.

As used herein, a promoter refers to a DNA sequence recognized by the synthetic machinery of the cell, or introduced synthetic machinery, required to initiate the specific transcription of a gene. Suitable promoters include, but are not limited to, RNA pol I, pol II, pol III, and viral promoters (e.g., human cytomegalovirus (CMV) immediate early gene promoter, the SV40 early promoter, and the Rous sarcoma virus long terminal repeat).

In certain embodiments, the promoter operably linked to a polynucleotide encoding a nucleic acid of the present invention can be an inducible promoter. Inducible promoters are known in the art and include, but are not limited to, the tetracycline promoter, the metallothionein IIA promoter, the heat shock promoter, the steroid/thyroid hormone/retinoic acid response elements, the adenovirus late promoter, and the inducible mouse mammary tumor virus LTR.

Methods of delivering expression constructs and nucleic acids to cells are known in the art and can include, by way of non-limiting example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

An aspect of the present invention provides a host cell comprising any herein-described nucleic acid of the present invention.

Another aspect of the present intention provides a method for inhibiting miR-22. The method comprising contacting miR-22 with a miR-22 inhibitory composition that is any herein-described nucleic acid of the present invention. The method may be in vitro or in vivo.

In another aspect, the present invention provides a pharmaceutical composition comprising any herein-described nucleic acid of the present invention and a pharmaceutically acceptable excipient or carrier.

Where clinical applications are contemplated, pharmaceutical compositions may be prepared in a form appropriate for the intended application. Generally, this will entail preparing compositions that are essentially free of pyrogens, as well as other impurities that could be harmful to humans or animals.

In one embodiment, a pharmaceutical composition comprises an effective dose of any herein-described nucleic acid of the present invention. An effective dose is an amount sufficient to affect a beneficial or desired clinical result. An effective dose may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of metabolic disorder, and nature of inhibitor or agonist (non-limiting examples include antagomir, expression construct, antisense oligonucleotide, polynucleotide duplex, etc.). Therefore, dosages can be readily ascertained by those of ordinary skill in the art from this disclosure and the knowledge in the art. For example, doses may be determined with reference Physicians' Desk Reference, 66th Edition, PDR Network; 2012 Edition (Dec. 27, 2011), the contents of which are incorporated by reference in its entirety.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the any herein-described nucleic acid of the present invention. Commercially available fat emulsions that are suitable for delivering the nucleic acids of the disclosure to adipose tissues (e.g., adipocytes) include INTRALIPIDO, LIPOSYN®, LIPOSYN® II, LIPOSYN® III, Nutrilipid, and other similar lipid emulsions. A colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965;

6,127,170; 5,837,533; 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising any herein-described nucleic acid of the present invention (e.g., liposomes or other complexes or expression vectors) dissolved or dispersed in a pharmaceutically acceptable carrier or aqueous medium. The phrases pharmaceutically acceptable or pharmacologically acceptable refer to molecular entities and compositions that do not produce adverse, allergic, or other untoward reactions when administered to an animal or a human. As used herein, pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The pharmaceutical forms, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating any herein-described nucleic acid of the present invention in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions may be administered in a manner compatible with the dosage formulation and in such amount as is therapeutically effective.

EXAMPLES

In order that the invention disclosed herein may be more efficiently understood, examples are provided below. It should be understood that these examples are for illustrative purposes only and are not to be construed as limiting the invention in any manner.

Example 1: Design of Anti-miR-22 Locked Nucleic Acid (LNA) Constructs

All the LNA anti-miR-22 are useful in both human and mouse. Host gene showed a 49% complementarity between human and mouse and LNA anti HG-miR-22 works predominately in human.

The constructs were designed to cover the seed sequence, contain between 8 nt and 20 nt in length, have a length-specific fraction of LNAs allowed and as high a binding affinity to miR-22 as possible (See FIGS. 1 and 2A-C).

Design elements included at least 2 LNA modifications at the end of the construct. Further design elements included no more than 4 LNA modifications in a row. Further still design elements included no more than 3 unmodified residues in a row.

Figure 3:
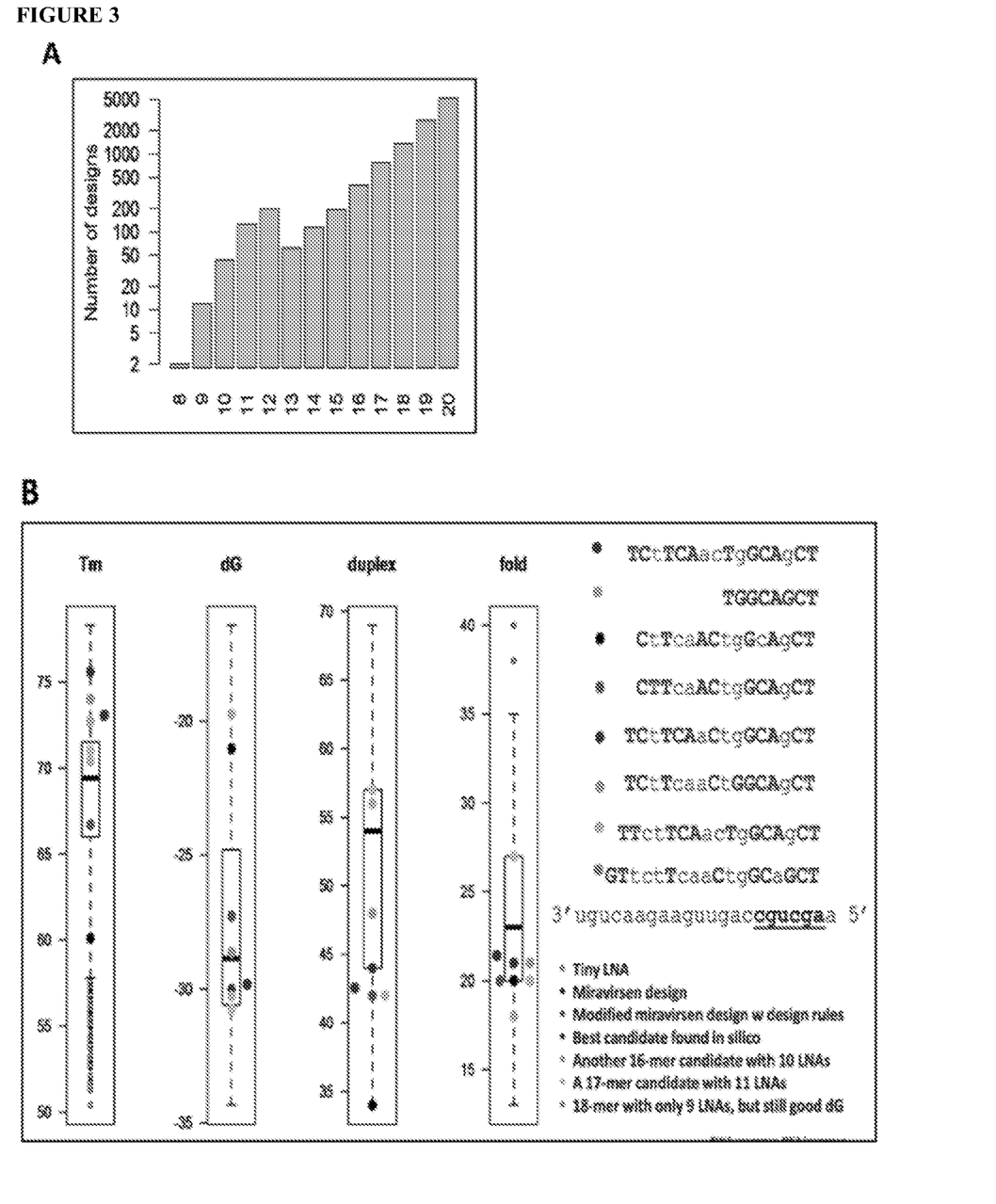
FIG. 3A-B shows the generation of possible anti-miR designs in silico (11228) and predict properties to select most optimal anti-miR-22 designs (8-18 nt in length). SEQ ID NO: 11, SEQ ID NO: 2, SEQ ID NO: 7 to SEQ ID NO: 10, SEQ ID NO: 12, SEQ ID NO: 13, and SEQ ID NO: 1 are shown, moving from top to bottom of the legend of FIG. 3B.
Figure 4:
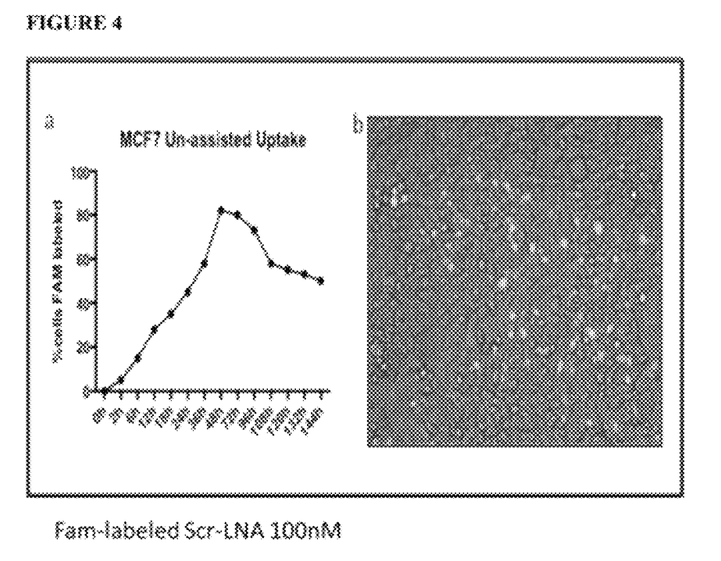
FIG. 4 shows an unassisted uptake in MCF7 of FAM-labeled LNA.
Figure 5:
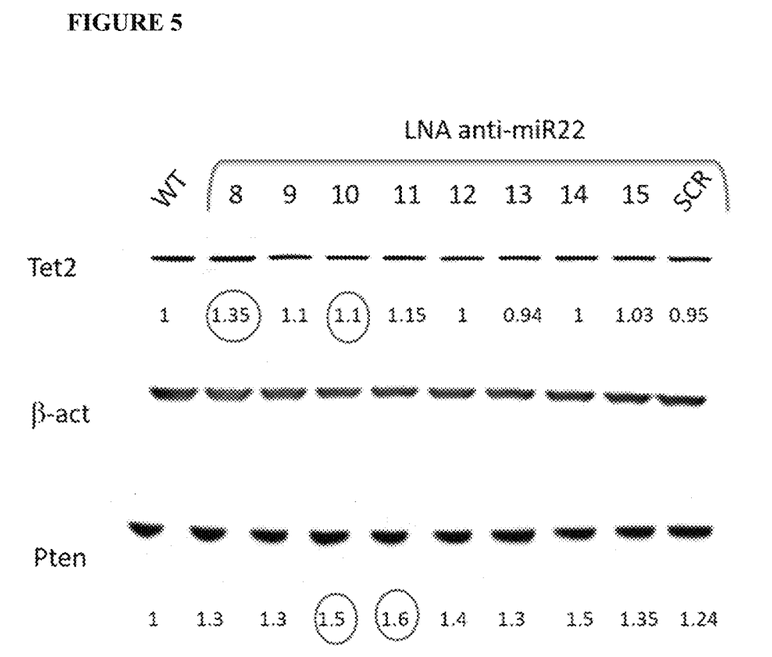
FIG. 5 is a western blot showing the validation of anti-miR-22 LNAs in MCF7 cells.
Figure 6:
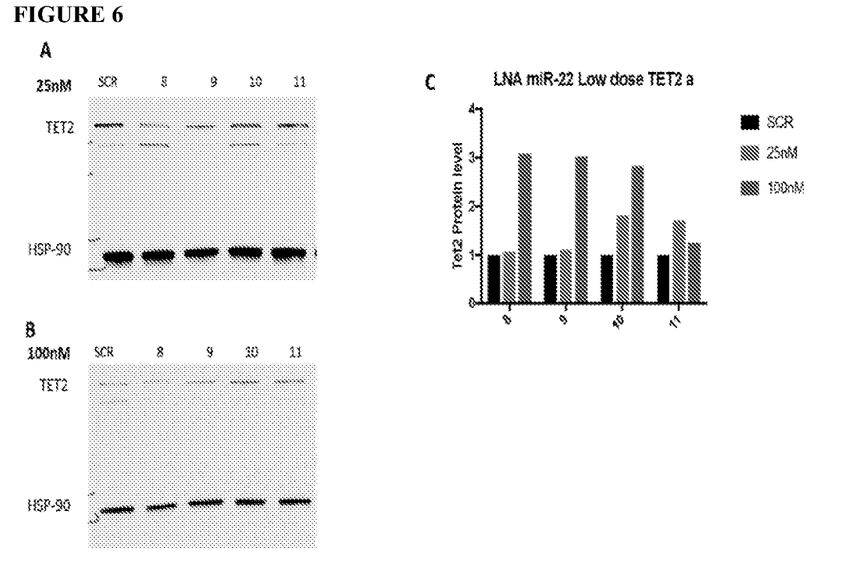
Figure 7:
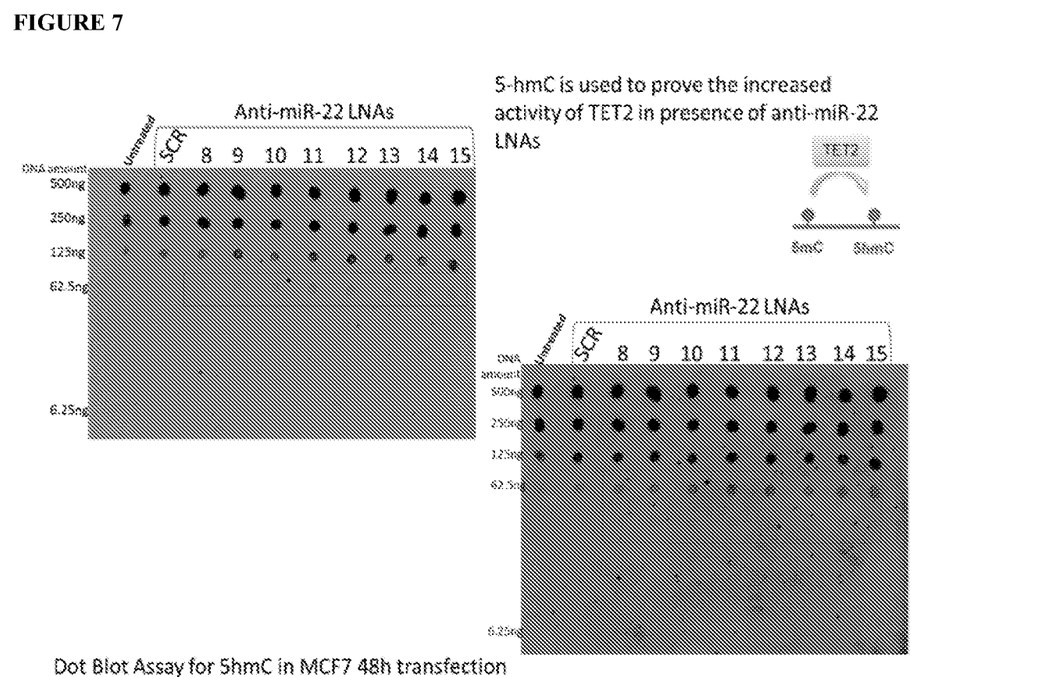
FIG. 7 is a pair of dot-blot images showing that anti-miR-22 LNAs increase the level of 5-hmC in MCF7.

The constructs were designed to bind to miR-22 with sufficient affinity to inhibit it. Also, the constructs were designed to have limited or no self-binding affinity (e.g. no or limited duplex or fold structures). See FIGS. 3A-B.

Figure 1:
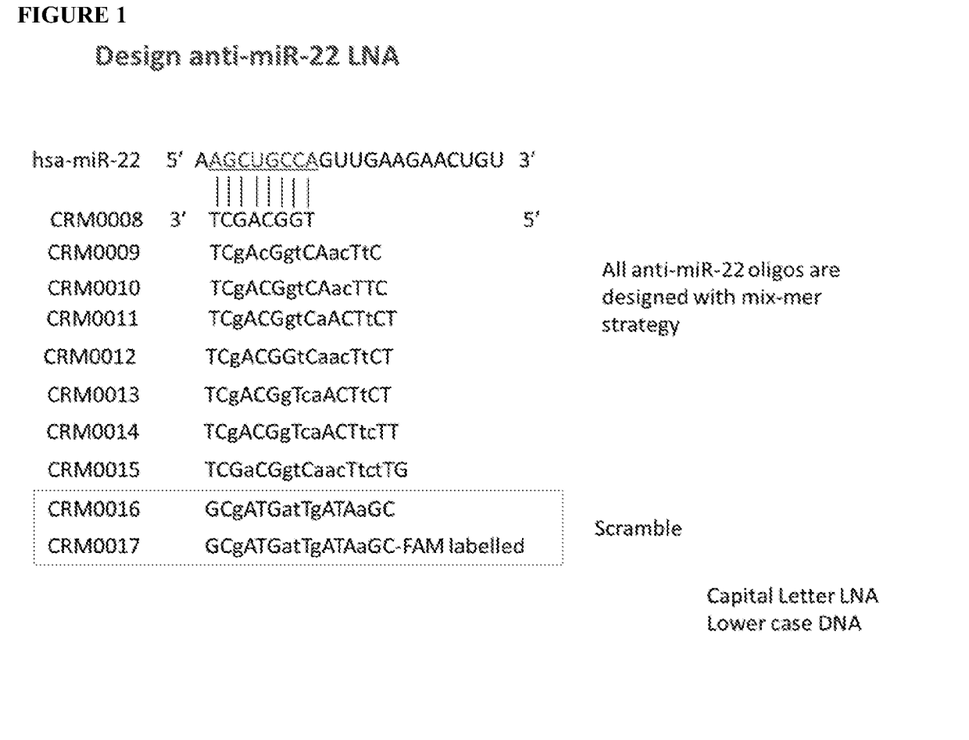
FIG. 1 shows the design of anti-miR-22 LNA. SEQ ID NO: 1, SEQ ID NO: 2, and SEQ ID NO: 7 to SEQ ID NO: 15 are shown.
Figure 2:
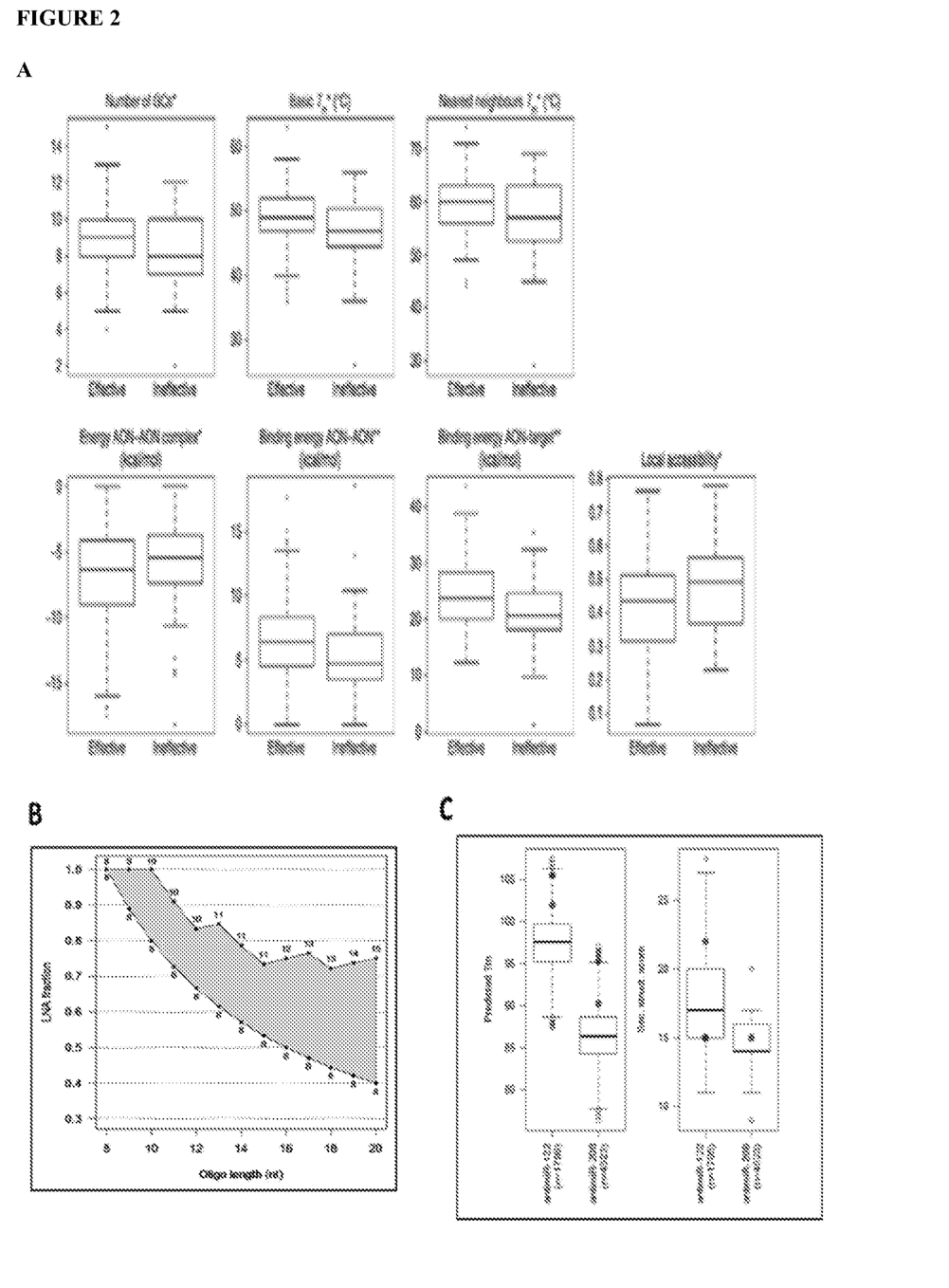
FIG. 2A-C are a series of bar graphs and a line graphs that show the design space for anti-miR-22 oligonucleotides.

In the below sequences, capital letters are LNA-modified and lower-case letters are unmodified; the orientations for the miR-22 (SEQ ID NO: 1) and for the anti-miR-22 oligonucleotides (SEQ ID NO: 2 and SEQ ID NO: 7 to SEQ ID NO: 13) are orientated 5' to 3'. FIG. 1 shows the anti-miR-22 oligonucleotides orientated 3' to 5' as they would be when hybridizing to miR-22. The oligonucleotides of SEQ ID NO: 14 and SEQ ID NO: 15, orientated 5' to 3', are scrambled sequences and do not hybridize to the miR-22 (SEQ ID NO: 1).

| hsa-miR-22 | AAGCUGCCAGUUGAAGAACUGU | (SEQ ID NO: 1) |
|---|---|---|
| CRM0008 | TGGCAGCT | (SEQ ID NO: 2) |
| CRM0009 | CtTcaACtgGcAgCT | (SEQ ID NO: 7) |
| CRM0010 | CTTcaACtgGCAgCT | (SEQ ID NO: 8) |
| CRM0011 | TCtTCAaCtgGCAgCT | (SEQ ID NO: 9) |
| CRM0012 | TCtTcaaCtGGCAgCT | (SEQ ID NO: 10) |
| CRM0013 | TCtTCAacTgGCAgCT | (SEQ ID NO: 11) |
| CRM0014 | TTctTCAacTgGCAgCT | (SEQ ID NO: 12) |
| CRM0015 | GTtctTcaaCtgGCaGCT | (SEQ ID NO: 13) |
| CRM0016 | CGaATAgTtaGTAgCG | (SEQ ID NO: 14) |
| CRM0017 | FAM labelled-CGaATAgTtaGTAgCG | (SEQ ID NO: 15) |

Example 2: Inhibition of miR-22

The ability of the constructs of Example 1 to inhibit miR-22 was assessed.

The sequences were validated in an assay by optimization of protocol for LNA assisted uptake (Lipo200 transfection), an adherent cell line, FAM labeled LNA was used and the biological effect validated by Identifying the most potent anti-miR-22 in adherent cell line assisted and un-assisted uptake (analysis of miR-22 level pre and post treatment and TET2 activity and protein level). The aim was to use the anti-miR in a mouse model with the most potent anti-miR for use for in-vivo treatment, see FIGS. 3A-B, FIG. 4, FIG. 5, FIG. 6, and FIG. 7 for confirmation results.

Further validation of the ability of the constructs of Example 1 to inhibit miR-22 was assessed in vivo in an obesity model.

Figure 8:
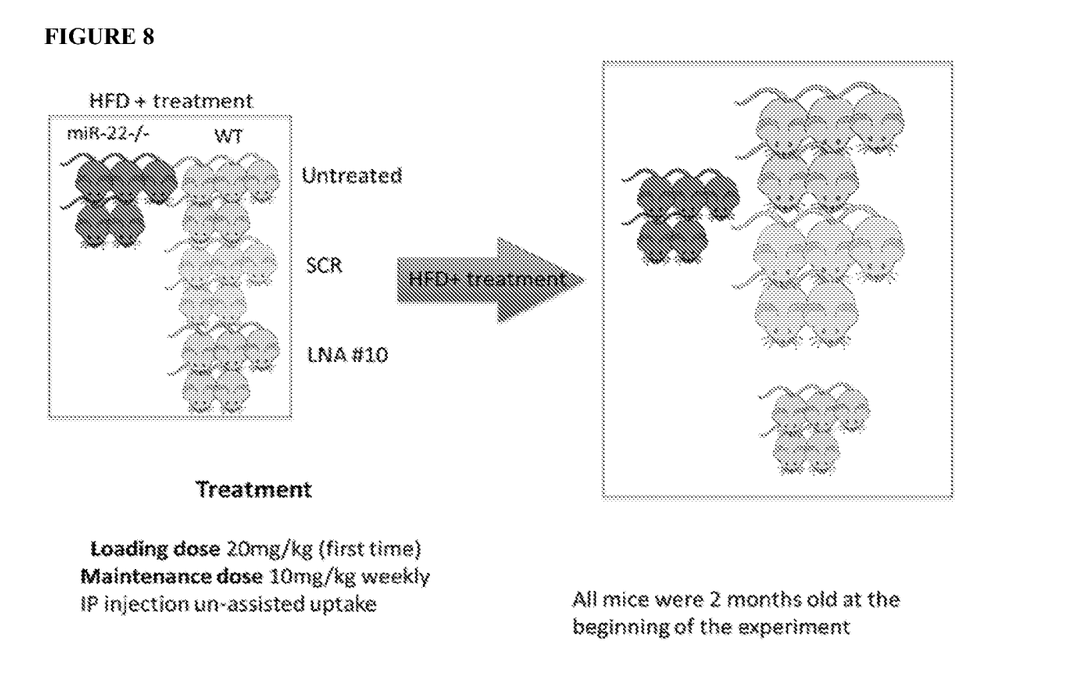
FIG. 8 is a pictorial showing the in vivo experimental planning and conditions for miR-22−/− and WT mice on HFD following transfection of Vehicle (VCH), Scramble Control RNA (SCR) and Locked Nucleic Acid (LNA).
Figure 9:
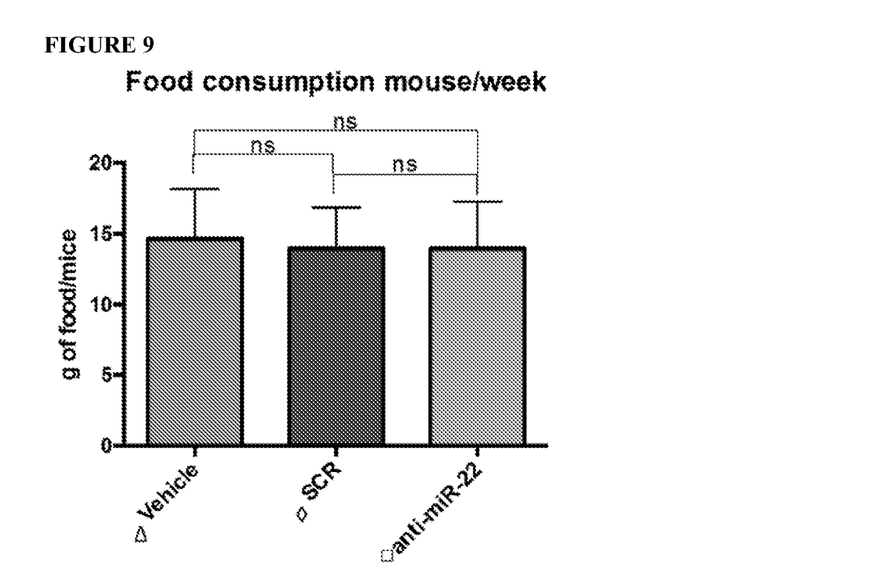
FIG. 9 is a bar graph showing that there is no difference between treated and non-treated mice in food consumption for (Δ) Vehicle, (◆) SCR, (■) anti-miR-22.
Figure 10:
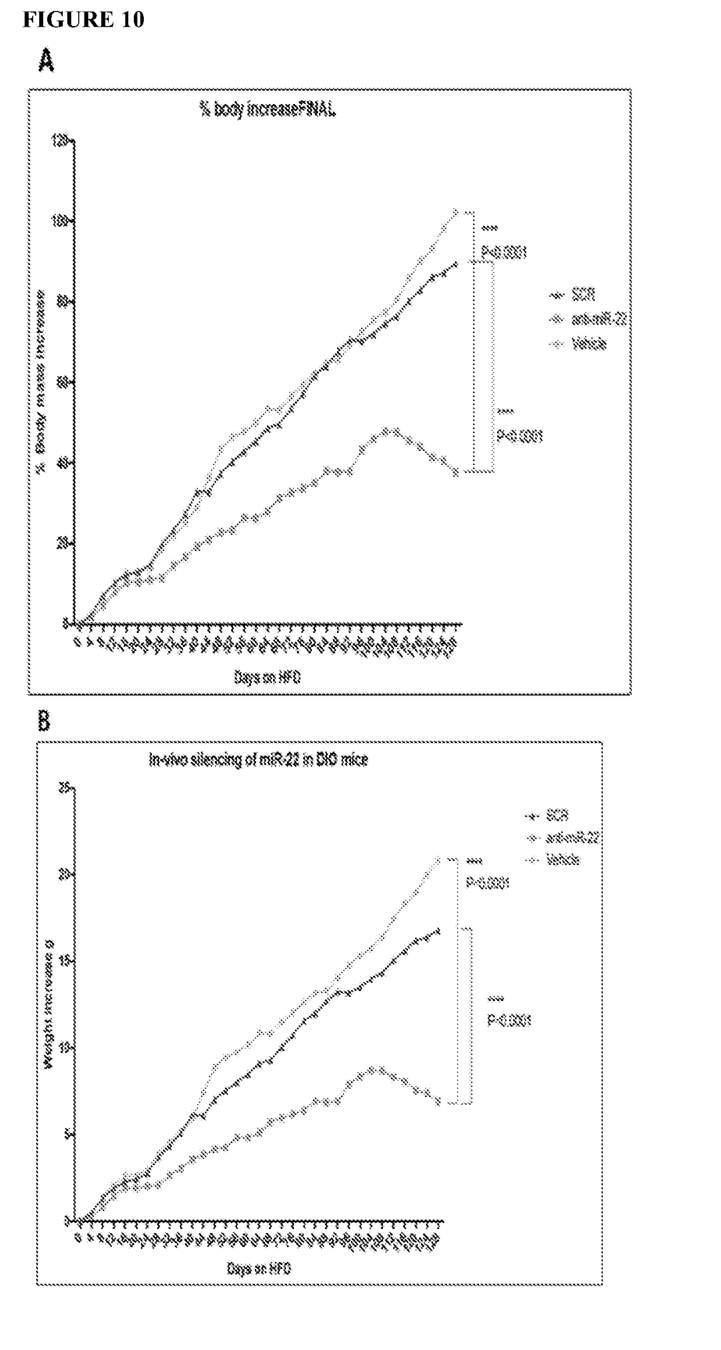

In an in vivo experimental planning for prevention, see FIG. 8, 2 months old miR-22−/− and WT on HFD were transfected with Vehicle (VCH), Scramble Control RNA (SCR) and a Locked Nucleic Acid (LNA) of Example 1 and treated with a Loading dose 20 mg/kg (first time) and a Maintenance dose 10 mg/kg weekly IP injection un-assisted uptake. There was no difference between treated and non-treated mice in food consumption, see FIG. 9. In vivo pharmacological inhibition of miR-22 prevented mice from becoming obese. See FIG. 10A-B.

Figure 11:
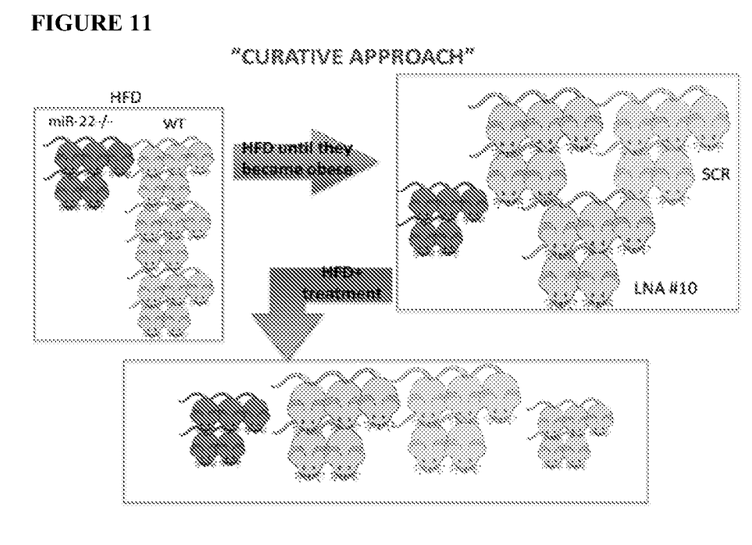
FIG. 11 is a pictorial of a curative approach showing miR-22 −/− and WT mice on a HFD treated with an anti-miR-22-LNA, SCR and a VHL and placed on a second HFD regimen.
Figure 12:
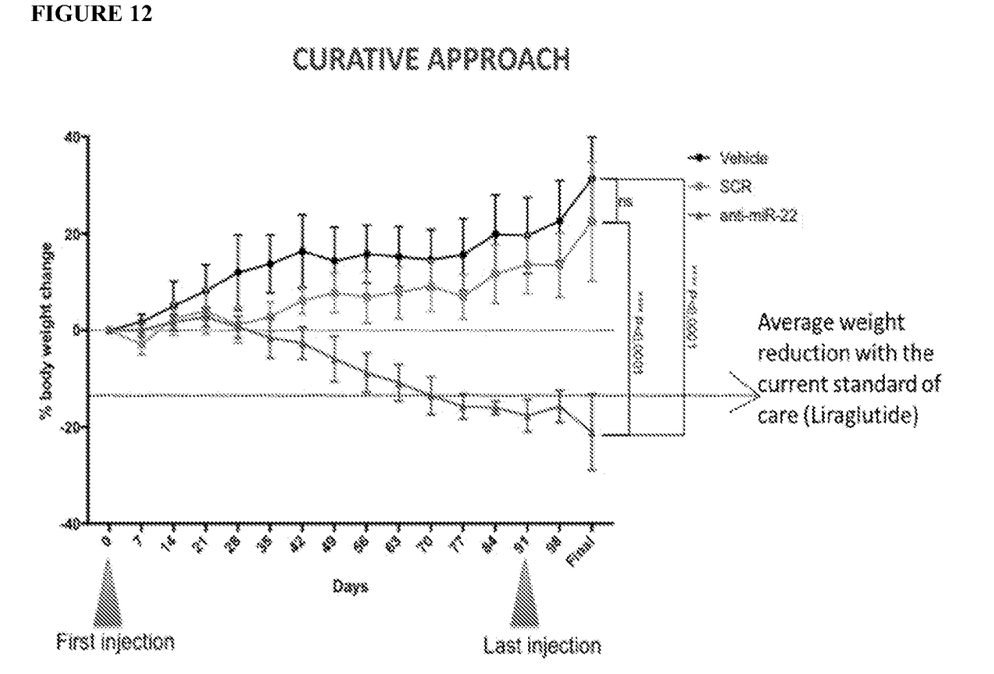
FIG. 12 is a line graph showing the results of the curative approach whereby there is a significant reduction in body weight in mice already obese and fed with a HFD. After 3½ months of treatment, a significant reduction in body weight was observed in obese mice (average weight >40 g) and fed with HFD. Mice were sacrificed, tissue collected, RNA from livers used for RNAseq.

FIG. 11 is a pictorial of a curative approach showing miR-22 −/− and WT mice on a HFD treated with an anti-miR-22-LNA, SCR and a VHL and placed on a second HFD regimen. As shown in FIG. 12, a construct of Example 1 inhibited miR-22, as evidenced by weight loss.

Figure 13:
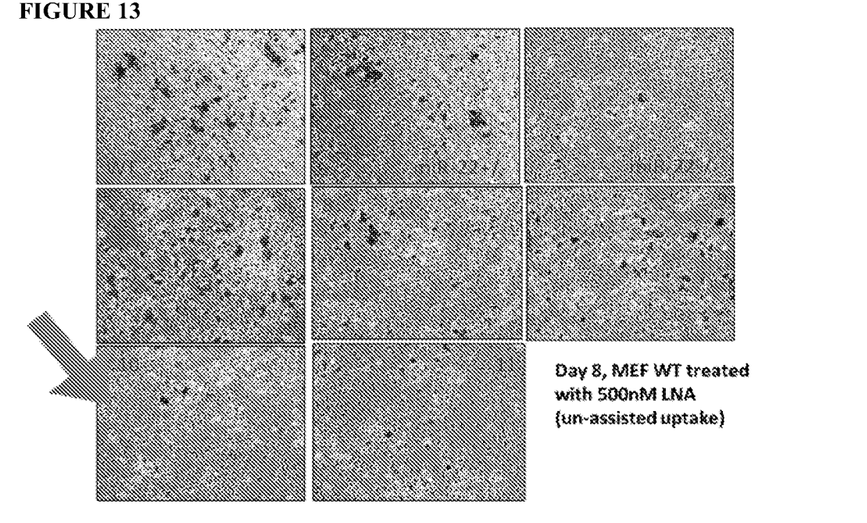
FIG. 13 is an Oil-Red-O staining showing that pharmacological inhibition of miR-22 is effective in impairing MEFs adipocytic differentiation.
Figure 14:
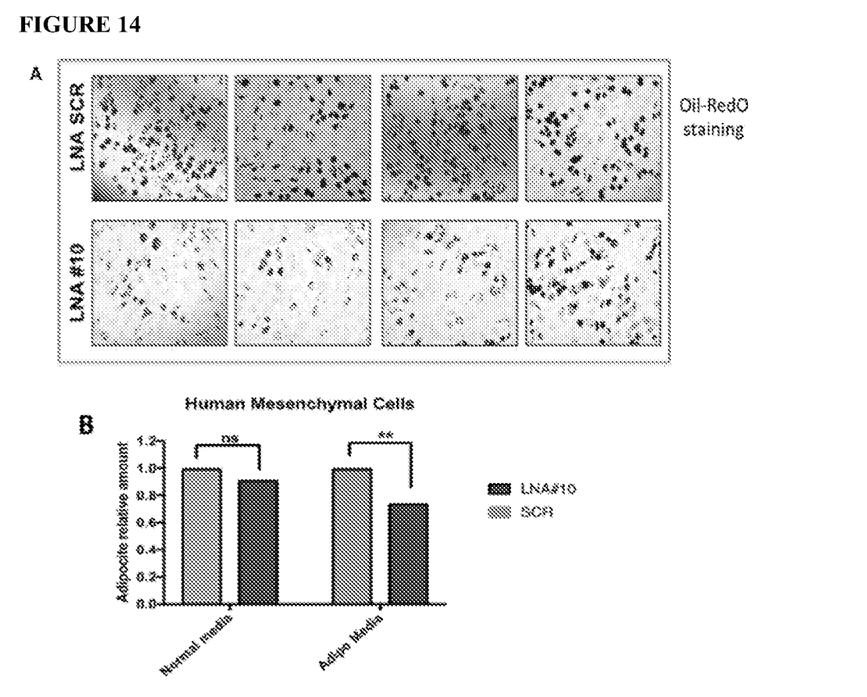
Figure 15:
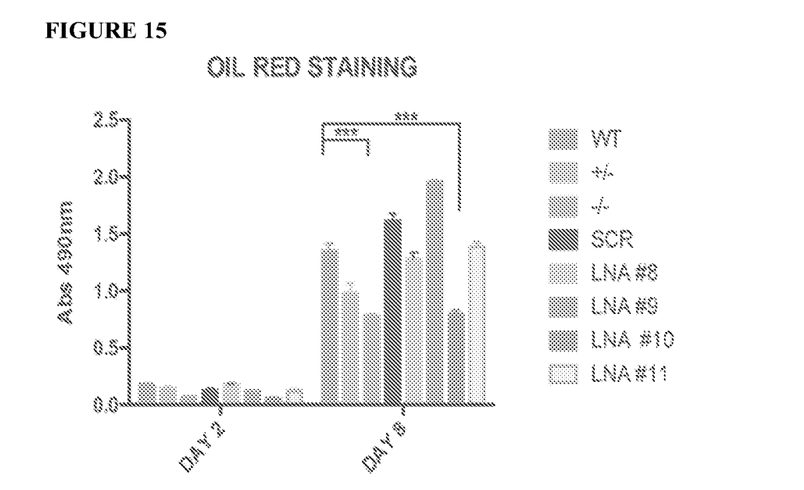
FIG. 15 is a bar graph showing that pharmacological inhibition of miR-22 is effective in impairing MEFs adipocytic differentiation. The order of data in the bar graphs, when reading from left to right corresponds with the legend (at the right of the graph) when reading from top to bottom.

Further evidence of miR-22 inhibition was seen in Oil-Red-O staining experiments that show impairing MEFs adipocytic differentiation. FIG. 13 shows that pharmacological inhibition of miR-22 with the constructs of Example 1 is effective in impairing MEFs adipocytic differentiation. FIG. 14 is an Oil-Red 0 staining (FIG. 14A) and a bar graph (FIG. 14B) showing that anti-miR-22 treatment in Human Primary Mesenchymal cells cultured in Adipo differentiation media for 2 weeks with or without LNA anti-miR-22. Un-assisted uptake 500 nM (LNAs added every 2 days). In FIG. 14B, the data in the right (red) bars in each bar graph is for the with LNA #10-treated cells. FIG. 15 is a bar graph showing that pharmacological inhibition of miR-22 is effective in impairing MEFs adipocytic differentiation. The order of data in the bar graphs, when reading from left to right corresponds with the legend (at the right of the graph) when reading from top to bottom. The number of LNAs corresponds to Example 1 above.

Accordingly, the nucleic acid constructs of Example 1 are effective in inhibiting miR-22.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any way.

What is claimed is:

1. A miR-22 inhibitor comprising a nucleic acid having a sequence consisting of CTTcaACtgGCAgCT (SEQ ID NO: 8) wherein the capital letters are LNA (locked nucleic acid) nucleotides, and the lower-case letters are DNA nucleotides.

2. A pharmaceutical composition comprising the nucleic acid of claim 1 and a pharmaceutically acceptable excipient or carrier.

3. A vector or plasmid comprising the nucleic acid of claim 1.

4. A host cell comprising the nucleic acid according to claim 1.

5. A method for inhibiting miR-22 comprising contacting miR-22 with a miR-22 inhibitor according to claim 1.

* * * * *

SEQUENCE LISTING

```
<160> NUMBER OF SEQ ID NOS: 15

<210> SEQ ID NO 1
<211> LENGTH: 22
<212> TYPE: RNA
<213> ORGANISM: Homo sapiens

<400> SEQUENCE: 1
aagcugccag uugaagaacu gu                                              22

<210> SEQ ID NO 2

<400> SEQUENCE: 2

000

<210> SEQ ID NO 3
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 3
cttcaactgg cagct                                                      15

<210> SEQ ID NO 4
<211> LENGTH: 16
```

```
<212> TYPE: DNA
<213> ORGANISM: Artificial Sequence
<220> FEATURE:
<223> OTHER INFORMATION: Synthetic Nucleic Acid

<400> SEQUENCE: 4
tcttcaactg gcagct                                                          16

<210> SEQ ID NO 5
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 5
ttcttcaact ggcagct                                                         17

<210> SEQ ID NO 6
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 6
gttcttcaac tggcagct                                                        18

<210> SEQ ID NO 7
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 7
cttcaactgg cagct                                                           15

<210> SEQ ID NO 8
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 8
cttcaactgg cagct                                                           15

<210> SEQ ID NO 9
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 9
tcttcaactg gcagct                                                          16

<210> SEQ ID NO 10
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 10
```

```
tcttcaactg gcagct                                                    16

<210> SEQ ID NO 11
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 11
tcttcaactg gcagct                                                    16

<210> SEQ ID NO 12
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 12
ttcttcaact ggcagct                                                   17

<210> SEQ ID NO 13
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 13
gttcttcaac tggcagct                                                  18

<210> SEQ ID NO 14
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 14
cgaatagtta gtagcg                                                    16

<210> SEQ ID NO 15
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 15
cgaatagtta gtagcg                                                    16
```